(12) United States Patent
Browka et al.

(10) Patent No.: US 9,585,812 B2
(45) Date of Patent: Mar. 7, 2017

(54) TRANSFER DEVICE WITH FLUID FILTER

(71) Applicant: YUKON MEDICAL, LLC, Morrisville, NC (US)

(72) Inventors: Edward P. Browka, Chapel Hill, NC (US); Theodore J. Mosler, Raleigh, NC (US); Gianni Guala, Turin (IT)

(73) Assignee: YUKON MEDICAL, LLC, Durham, NC (US)

( * ) Notice: Subject to any disclaimer, the term of this patent is extended or adjusted under 35 U.S.C. 154(b) by 390 days.

(21) Appl. No.: 14/377,437

(22) PCT Filed: Feb. 7, 2013

(86) PCT No.: PCT/US2013/025163
§ 371 (c)(1),
(2) Date: Aug. 7, 2014

(87) PCT Pub. No.: WO2013/119823
PCT Pub. Date: Aug. 15, 2013

(65) Prior Publication Data
US 2015/0250680 A1 Sep. 10, 2015

Related U.S. Application Data

(60) Provisional application No. 61/595,877, filed on Feb. 7, 2012.

(51) Int. Cl.
*A61B 19/00* (2006.01)
*A61M 39/22* (2006.01)
*A61J 1/20* (2006.01)

(52) U.S. Cl.
CPC ............. *A61J 1/2086* (2015.05); *A61J 1/201* (2015.05); *A61J 1/2048* (2015.05); *A61J 1/2075* (2015.05);
(Continued)

(58) Field of Classification Search
CPC ........ A61J 1/2086; A61J 1/2048; A61J 1/201; A61J 1/2075; A61J 1/2096; A61J 1/2055; A61J 1/2037; A61J 1/2065
See application file for complete search history.

(56) References Cited

U.S. PATENT DOCUMENTS

2003/0109846 A1 6/2003 Zinger
2007/0079894 A1 4/2007 Kraus
(Continued)

FOREIGN PATENT DOCUMENTS

| DE | 3820204 A1 | 12/1989 |
|----|------------|---------|
| DE | 29913550 U1 | 11/1999 |
| WO | 03043564 A1 | 5/2003 |

OTHER PUBLICATIONS

European Patent Office; Extended European Search Report for European Application No. 13747273.4 dated Aug. 21, 2015, 7 Pages.
(Continued)

*Primary Examiner* — Leslie Deak
(74) *Attorney, Agent, or Firm* — Christopher J. Knors; Moore & Van Allen PLLC

(57) ABSTRACT

A vial access device is described comprising an upper housing having a fluid connector in fluid communication with the upper housing; a vial access spike projecting from the upper housing; a fluid filter body within the upper housing or connectable thereto, the fluid filter body in fluid communication with the vial access spike and the fluid connector. Methods of reducing or eliminating particulate matter from medicament solutions are also provided.

16 Claims, 15 Drawing Sheets

(52) U.S. Cl.
CPC .......... *A61J 1/2096* (2013.01); *A61M 39/223* (2013.01); *A61J 1/2037* (2015.05); *A61J 1/2055* (2015.05); *A61J 1/2065* (2015.05); *A61J 1/2082* (2015.05)

(56) References Cited

U.S. PATENT DOCUMENTS

| | | |
|---|---|---|
| 2007/0093775 A1 | 4/2007 | Daly |
| 2008/0172024 A1 | 7/2008 | Yow |
| 2011/0178493 A1 | 7/2011 | Okiyama |

OTHER PUBLICATIONS

The International Bureau of WIPO, International Application No. PCT/US2013/025163, International Preliminary Report on Patentability dated Aug. 21, 2014, 8 pages.

Korean Intellectual Property Office, International Application No. PCT/US2013/025163 International Search Report and Written Opinion dated May 24, 2013, pp. 1-13.

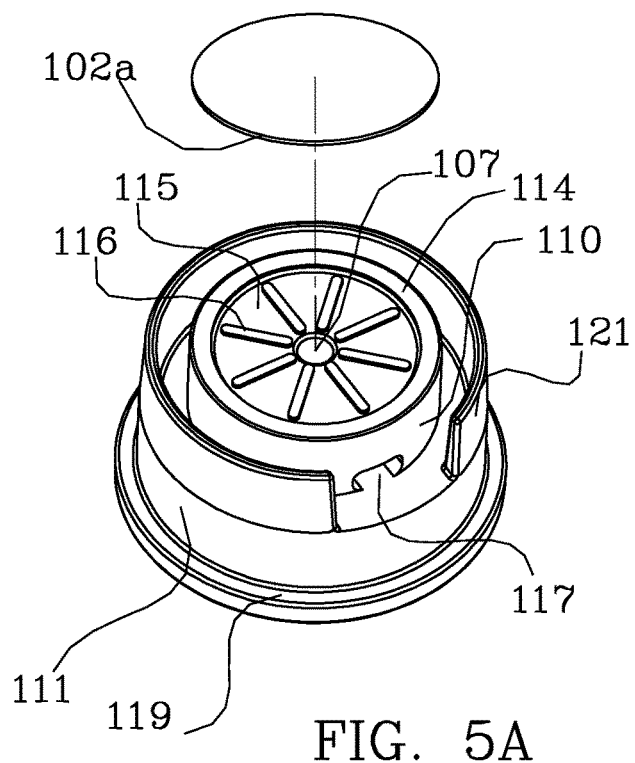
FIG. 5A
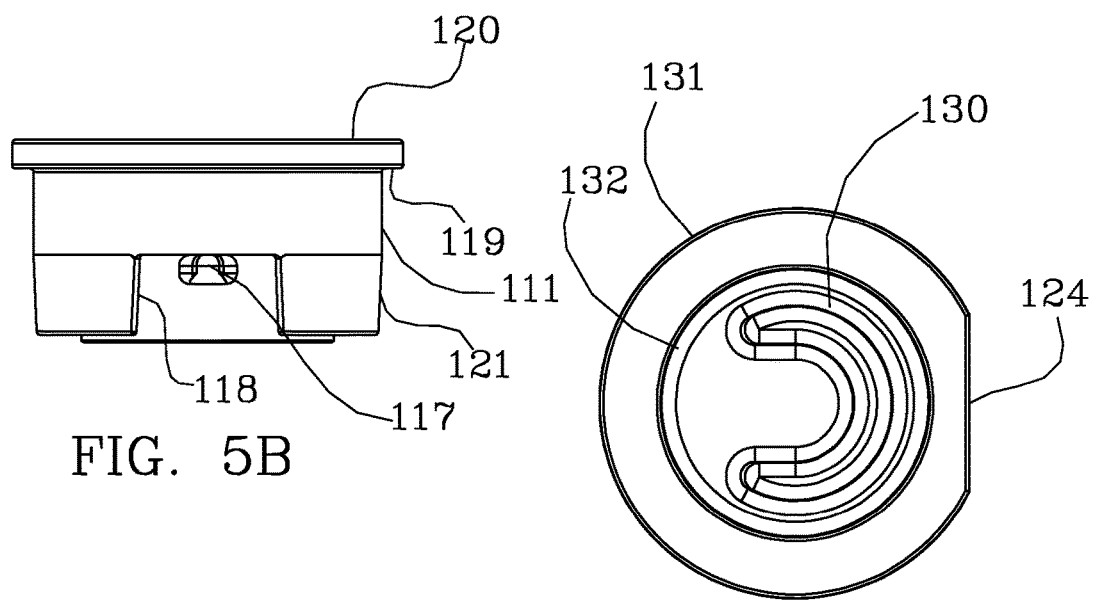
FIG. 5B
FIG. 5C

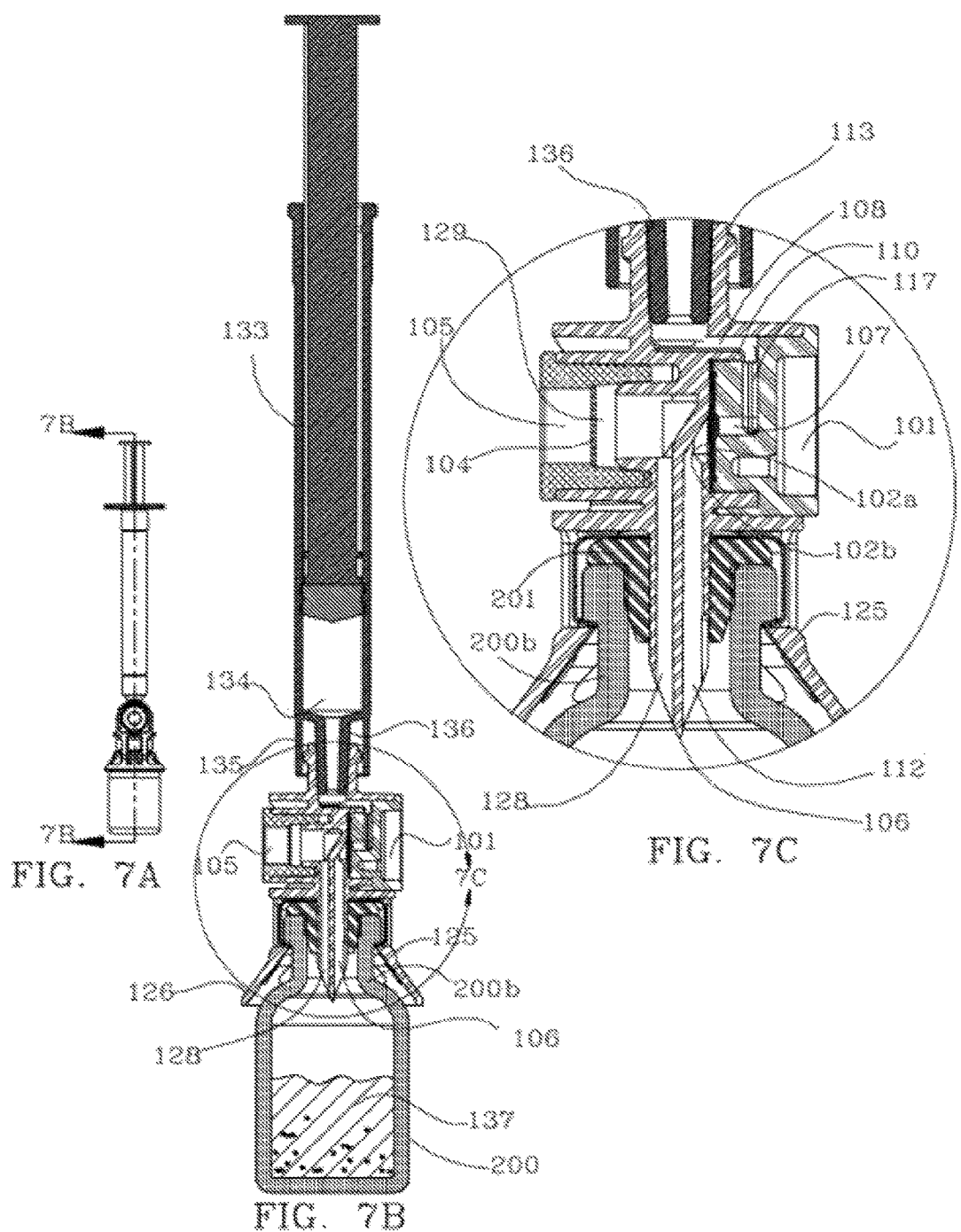

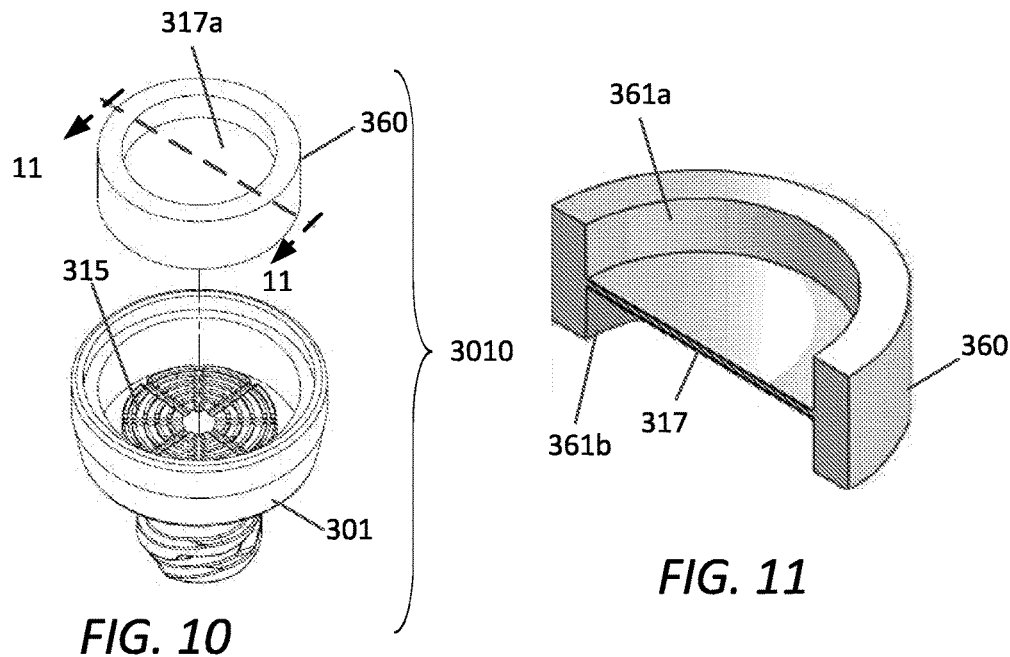
FIG. 10
FIG. 11
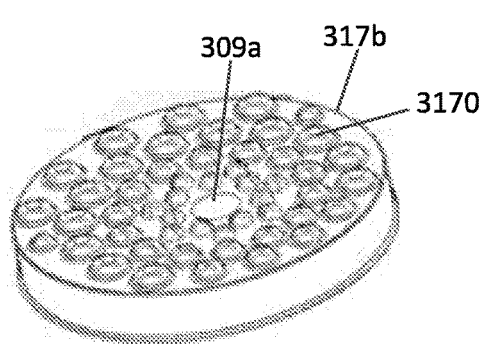
FIG. 12
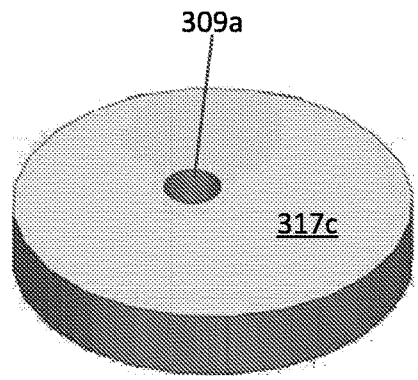
FIG. 13

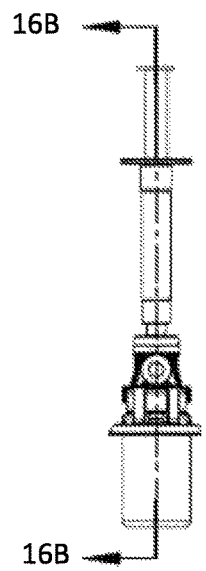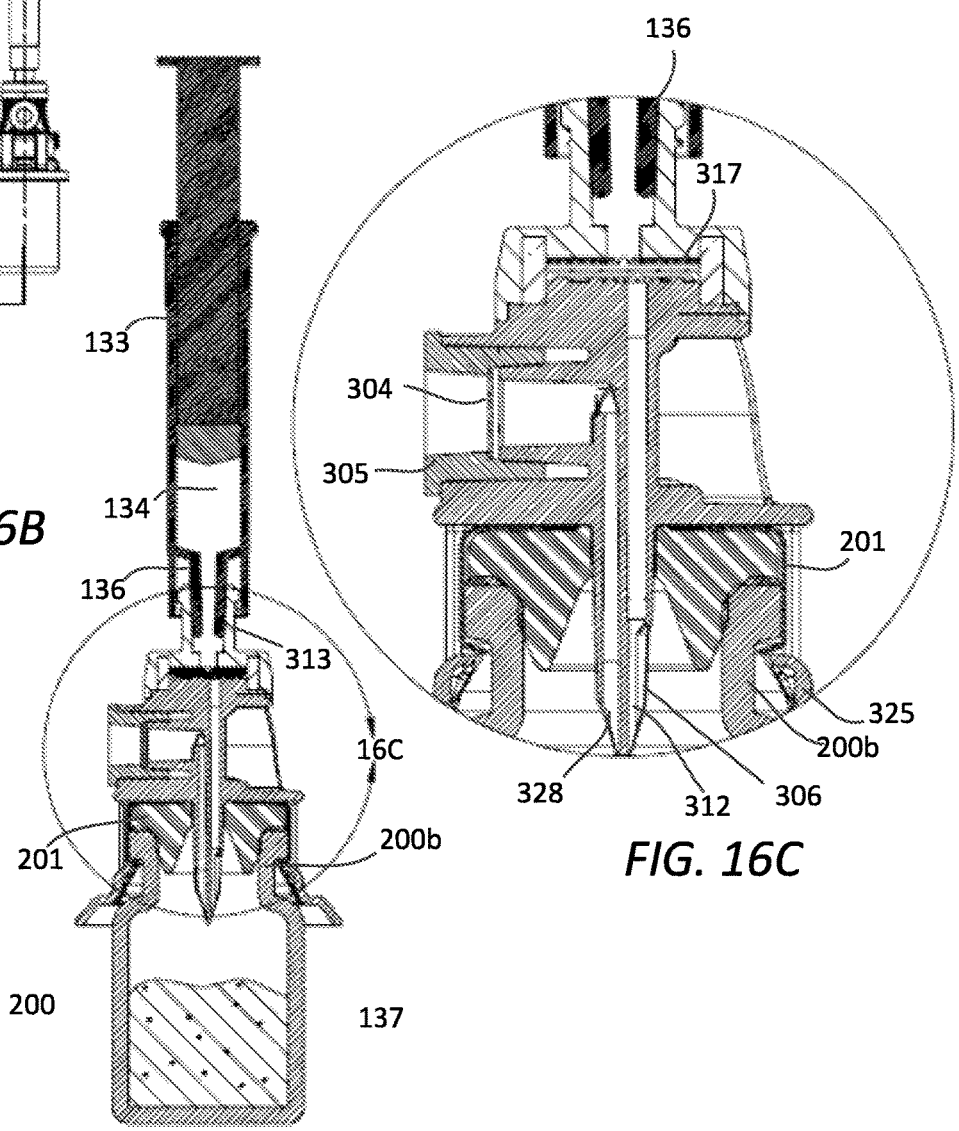

TRANSFER DEVICE WITH FLUID FILTER

CROSS-REFERENCE TO RELATED APPLICATIONS

This application is filed under the provisions of 35 U.S.C. §371 and claims the benefit of International Patent Application No. PCT/US2013/025163, filed on Feb. 7, 2013, which claims the benefit of U.S. Provisional patent application 61/595,877, filed in the United States Patent and Trademark Office on Feb. 7, 2012, all of which are hereby incorporated by reference in their entirety.

TECHNICAL FIELD

The present invention relates generally to transfer devices for use with medicinal substances. More particularly, the invention concerns a vial access device for connecting with a vial or container and to allow mixing and/or transfer of a fluid, the fluid being filtered upon transfer from the vial or container.

BACKGROUND

Liquid drugs are typically provided in medicament vials with standard elastomeric closure sizes, such as 20 mm and 13 mm diameter closures. Vial access devices are used to withdraw medication from these vials. Particulate may be present in the vial or become mixed in the medication during the fluid removal process. Types of particles that may be present in vials include; pharmaceutical sediment, lipids, un-dissolved solids, recrystallization of medication elements, glass, plastic and rubber debris, septum particulate and various other types of contaminants, these particles can be various sizes and shapes, and depending on the medicament, hydrophobic and/or hydrophilic, and/or partially or completely ionized salts. In addition, insertion of the vial access spike can shear off or core bits of the stopper of the vial. Often these particles are sub-visible sizes and will go unnoticed. Particulates that are injected into a patient can cause complications, for example, phlebitis, organ damage, and vessel blockage.

SUMMARY

In a first embodiment, a vial access device is provided, the vial access device comprising (i) an upper housing comprising: a connector member for receiving a medicament delivery device, the connector member having a fluid conduit in fluid communication with the upper housing; and a bottom surface; (ii) a spike having a proximal end and a distal end, the proximal end projecting from the bottom surface of the upper housing, the spike having at least one lumen arranged parallel to a first longitudinal axis, the at least one lumen connecting the proximal end of the spike with the distal end, the at least one lumen being in fluid communication with the upper body; configured to present fluid to the filter surface while flowing along the longitudinal axis; (iii) a fluid filter body for filtering particulate matter from fluid flowing through the at least one lumen, the fluid filter body comprising a fluid filter having a front surface to be contacted by fluid from the at least one lumen, the front surface aligned with the first longitudinal axis and substantially parallel to the direction of fluid flow in the at least one lumen, the fluid filter body further comprising a first fluid path in contact with a back surface of the fluid filter surface, the first fluid path non-parallel with the first longitudinal axis and connected to a second fluid path (108) the second fluid path connected with the fluid conduit of the connector member; (iv) optionally, a vent body and vent filter; and (v) a lower housing connected to the upper housing, the lower housing having a shroud projecting therefrom and at least partially surrounding a portion of the spike; the shroud configured to receive a vial or container.

In a third embodiment, a vial access device is provided, the vial access device comprising: an upper housing having a fluid connecter in fluid communication with the upper housing; a vial access spike projecting from the upper housing; and a fluid filter body within the upper housing, the fluid filter body in fluid communication with the vial access spike and the fluid connector, the fluid filter body having a fluid filter surface substantially parallel to the direction of fluid flow through the access spike.

In a fourth embodiment, a vial access device is provided, the vial access device comprising A vial access device comprising (i) a fluid filter assembly comprising: a connector member for receiving a medicament delivery device, the connector member providing fluid communication with medicament delivery device; a housing containing a fluid filter; (ii) an upper housing receiving the fluid filter assembly at a top surface, the upper housing comprising: a spike having a longitudinal axis and a proximal end and a distal end, the proximal end projecting from a bottom surface of the upper housing, the spike having at least one lumen arranged parallel to the longitudinal axis, the at least one lumen connecting the proximal end of the spike with the distal end, the at least one lumen being in fluid communication with the fluid filter; and an opening receiving an vent filter body with vent filter; the fluid filter having a front surface aligned non-parallel with the longitudinal axis and substantially perpendicular to the direction of fluid flow in the at least one lumen, and the vent filter positioned non-parallel with the longitudinal axis; (iv) optionally, a shroud projecting therefrom and at least partially surrounding a portion of the spike; the shroud configured to receive a vial or container.

In a fifth embodiment, a method of filtering particulate material from a medicament is provided, the method comprising providing a vial access device as defined in the first embodiment and optionally, providing at least one of a vial comprising reconstituted or reconstitutable medicament and/or a delivery device selected from a syringe, IV bag, or IV line.

BRIEF DESCRIPTION OF THE DRAWINGS

FIG. 5A is a perspective view of a filter body as disclosed and described herein.

FIG. 5B is a perspective side view of the filter body of FIG. 5A.

FIG. 5C is a top view of the filter body of FIG. 5A.

FIG. 7A is a side view of the vial access device embodiment of FIG. 1A shown operatively connected to a vial and syringe with sectional plane 7B-7B shown.

FIG. 7B is a side cross section view along sectional plane 7B-7B of the access device embodiment as configured in 7A.

FIG. 7C is a detail view of the fluid path and filter arrangement of the vial access embodiment of FIG. 7B

FIG. 10 is an exploded view of a filter assembly embodiment as disclosed and described herein.

FIG. 11 is a sectional view of the filter of FIG. 10 shown along sectional plane 11-11.

FIG. 12 is a filter embodiment as disclosed and described herein.

FIG. 13 is a filter embodiment as disclosed and described herein.

FIG. 16A is a side view of the vial access device embodiment of FIG. 9A shown operatively connected to a vial and syringe with sectional plane 16B-16B shown.

FIG. 16B is a side cross section view along sectional plane 16B-16B of the access device embodiment as configured in 16A.

FIG. 16C is a detail view of the fluid path and filter arrangement of the vial access embodiment of FIG. 16B FIG. 178A is a side view of the vial access device of embodiment of FIG. 9A shown operatively connected to a vial and syringe with sectional plane 17B-17B shown.

DETAILED DESCRIPTION

Figure 1A:
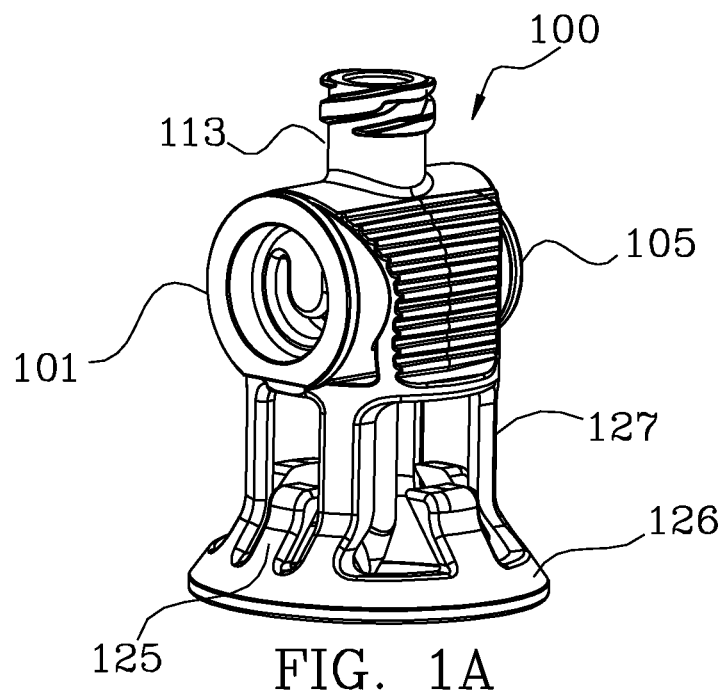
FIG. 1A Is a perspective view of a vial access device embodiment of the device shown fully assembled.

In one embodiment, a transfer device is provided that includes a filter for filtering particulate matter from a mixture contained in a vial or container. In one aspect, the mixture is a reconstituted medicament having suspended particulate matter, gels, insoluble material, and/or foreign matter.

A vial access device of the type disclosed and described can be used so that fluid withdrawn from the vial is filtered of particulate. Additionally the filter element is inexpensive to produce and adds minimal additional assemble cost or tooling complexity.

Aspects of the present disclosure provide a vial access device that is of a simple construction, can easily be used and inexpensively manufactured in large quantity. These and other features of the present disclosure are provided by the vial access device that will be described in the paragraphs that follow.

A vial access device is provided wherein the device comprises an upper housing that has a fluid connector, e.g., luer fitting or threaded assembly, etc., for the attachment of a fluid delivery device such as a syringe, and a hollow spike with at least one lumen (e.g., a vent and fluid lumen) projecting from a bottom surface of the upper housing, the spike allowing for penetration of an vial closure element and for providing fluid communication with the upper housing.

The upper body has a pair of receiving ports for receiving a fluid filter body housing and an air vent body housing. The fluid filter body housing comprises a first fluid conduit arranged non-parallel to the longitudinal axis of the spike and a second fluid conduit substantially parallel with the first conduit and in fluid communication with the fluid connector. Positioned between the spike lumen and the first fluid conduit of the fluid filter body is a fluid filter having a front and a back surface, the front surface arranged to be essentially parallel to the longitudinal axis of the flow of fluid from the spike lumen. Likewise, the air vent body housing comprises fluid conduits for aspirating and/or venting with the ambient and an vent filter. The vent filter has a front surface and a back surface, the front surface arranged essentially parallel to the spike lumen.

The bottom surface of the upper housing has a projecting wall or shroud at least partially surrounding the spike, the shroud having fingers projecting inwards towards the spike configured to hold a vial or container.

The vial access device described herein uses a simple single action tool to produce filter body and/or filter body. Assembly of the filter bodies into the upper housing is achieved with a single linear motion to a given force or distance. The filter body can be both keyed and include a reference flat to aid in and ensure part positioning during assembly. While it is possible to use welding to assemble the filter body with the upper housing, the double annular press fit design of the vial access device disclosed herein allows for seal fluid path to be created without the need for such secondary weld operations, simplifying assembly and reducing tooling costs to manufacture the device. In this configuration, minimal dead volume is created by fluid path and filter and/or minimal increase in resistance to flow. In certain aspects, cross sectional area of the flow path in the fluid filter body and/or upper housing is essentially consistent throughout its length. Turns in the flow path are smooth and radiused to reduce fluid drag. The configuration of the filter disk allows for a relatively large filter surface area in comparison to the overall device envelope.

Referring to the drawings and particularly to FIGS. 1, 2 and 3, one embodiment of the vial access device as disclosed for securing to a vial having a pierceable septum and allowing access and/or mixing and/or transference substances contained within the vial to form a mixture and/or remove the mixture into a delivery device for administration to a subject is illustrated.

Figure 1B:
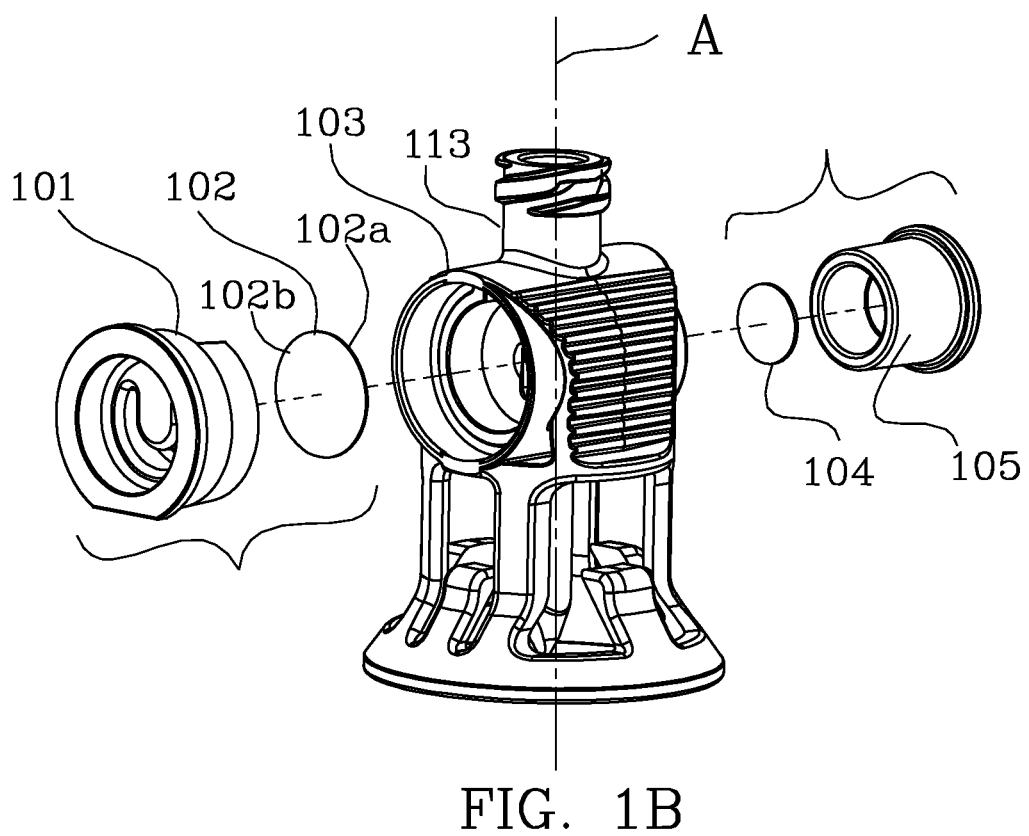
FIG. 1B Is an exploded perspective view of the vial access device of FIG. 1A as disclosed and described herein.

Referring to FIGS. 1A and 1B, are shown a perspective view of an embodiment of device 100, shown in a fully assembled state. FIG. 1B is an exploded perspective view along sectional plane 1B-1B showing fluid filter body 101 with fluid filter 102 assembled with upper housing 103. Also shown is vent filter body 105 with corresponding vent filter 104 assembled into upper housing 103.

Fluid filter 102 can consist of any appropriate material, micron porosity and efficiency for a given application. A typical range of micron porosity for a fluid filter is between about 0.2 uM and about 15 uM (micron). In one aspect, fluid filter 102 can be disk-shaped. Other shapes can be used for fluid filter 102.

Vent filter 104 can consist of any appropriate material, micron porosity and efficiency for a given application. A typical range of micron porosity for an vent filter is between 0.02 uM and 150 uM (micron). In one aspect, fluid filter 102 can be disk-shaped. Other shapes can be used for the vent filter 104.

Figures 2A, 2B:
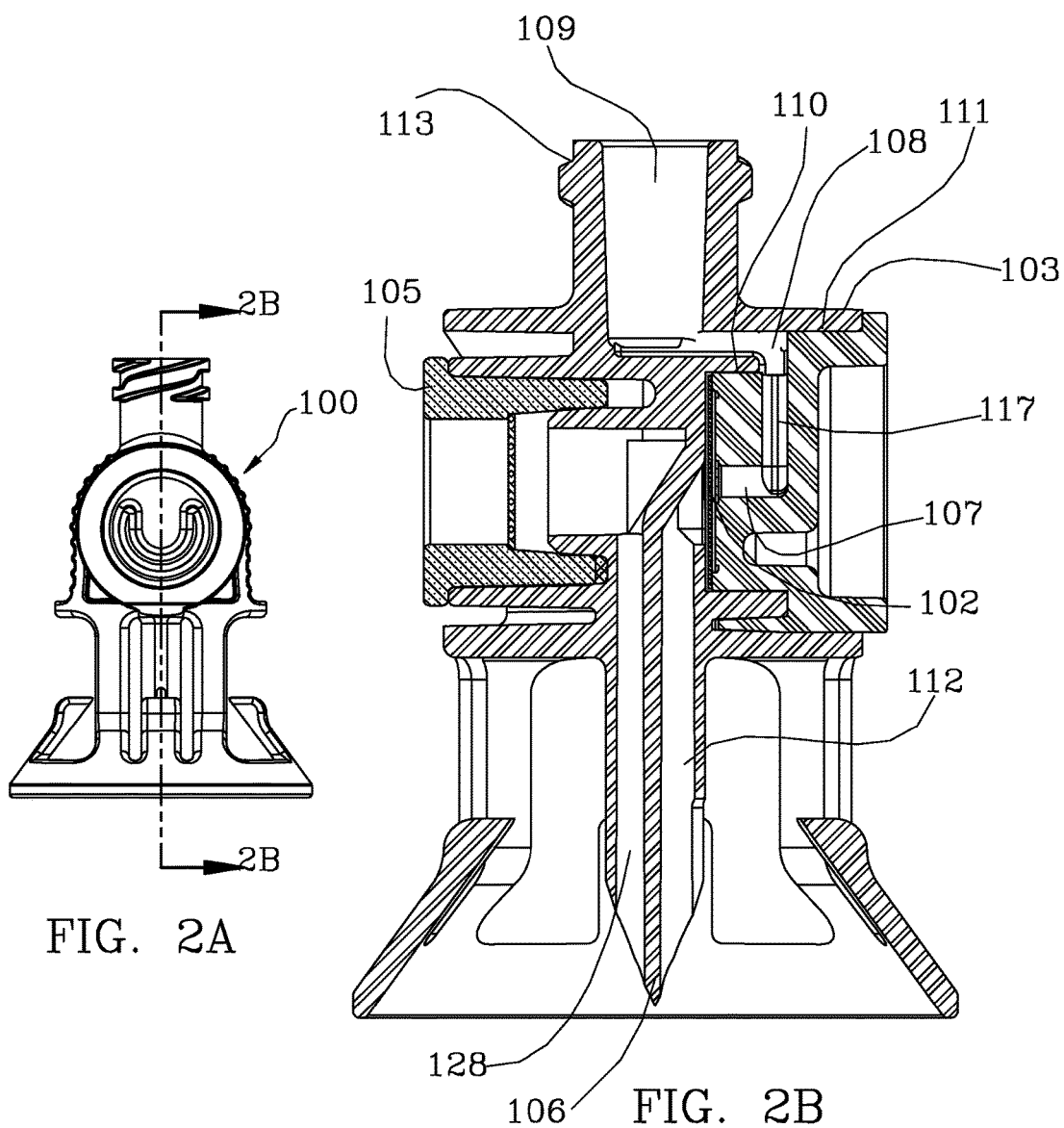
FIG. 2A is a side view showing sectional plane 2B-2B.
FIG. 2B is a side cross section view of the embodiment of FIG. 2A shown along section plane 2B-2B.

Referring to FIGS. 2A and 2B, FIG. 2A is a side view of device 100 and FIG. 2B is a side cross section view of the embodiment along sectional plane 2B-2B. Upper housing comprises connector member 113 having fluid conduit 109 in fluid communication with upper housing 103. Vial access spike 106 provides a fluid conduit 112 from spike 106, through fluid filter 102 and into first fluid conduit 107 in the filter body 101. First fluid conduit communicates with second fluid conduit 108 in upper housing 103 to fluid conduit 109 of connector member 113. In one aspect, fluid from a vial or connector is presented to a front surface of fluid filter 102, the front face being substantially parallel to the direction of fluid flow and substantially parallel to the longitudinal axis of spike 106. Spike 106 includes vent conduit 128 communicating with vent filter body 105 and ambient.

During use of device 100, the direction of fluid flow is generally to/from fluid conduit 112 of spike 106 to connector conduit 109, the force to induce flow is created by a delivery device (e.g., syringe) attached to connector member 113. Connector can be a luer fitting or other threaded connector. The cross sectional area of the fluid path does not change significantly over this span so as not to inhibit flow or create pressure gradients within the device. Surface 110 and fluid filter 102 separate unfiltered fluid conduit 112 from filtered fluid conduit 107 and form a seal between upper housing 103 and fluid filter body 101. Surface 110 can be generally annular in shape, square, rectangular, oval, etc., provided it is configured to form a seal with upper housing 103 via various means including press fit, solvent bond, adhesive bond, ultrasonic bond, and/or via an additional elastomeric element such as an o-ring.

The fluid filter 102 may be attached to the fluid filter body 101 via adhesive, ultrasonic welding or insert molding. Alternately the fluid filter may be held in place by a compression fit between the upper housing 103 and the fluid filter body 101 Alternately the fluid filter 102 may be attached to the upper housing by the assemble methods previously listed.

Figure 3A:
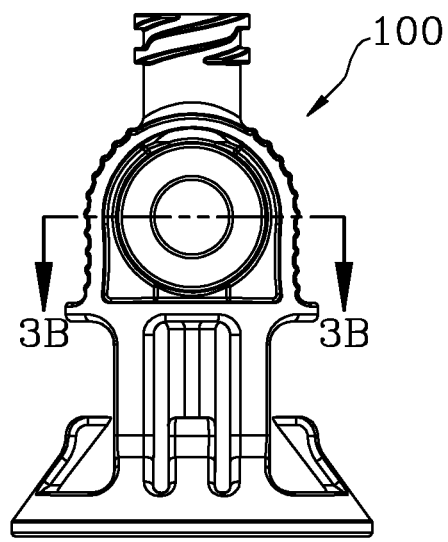
FIG. 3A is a perspective view of the embodiment of FIG. 2A rotated 180 degrees showing sectional plane 3B-3B.
Figure 3B:
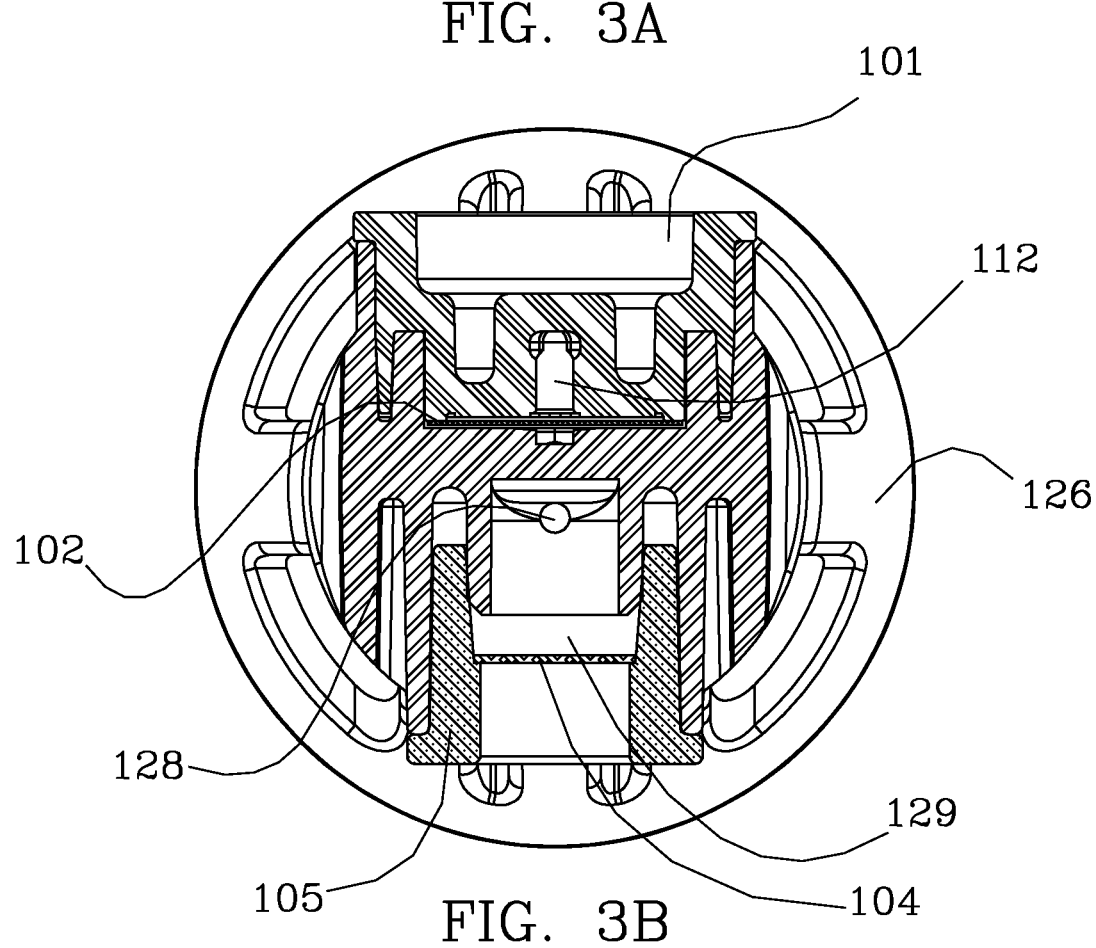
FIG. 3B is a cross section view of the embodiment of FIG. 3A shown along section plane 3B-3B, which is normal to the cross sectional plane 2B-2B.

Referring to FIGS. 3A and 3B, FIG. 3B is a cross section view of the embodiment of FIG. 2B along sectional plane 3B-3B, which is normal to the cross sectional plane 2B-2B of FIG. 2B. Fluid conduit 112 and vent conduit 128 are shown viewed down their respective longitudinal axes. Fluid filter body 101 and vent filter body 105 are shown in a press-fit or interference fit arrangement with upper housing 103.

Figure 4B:
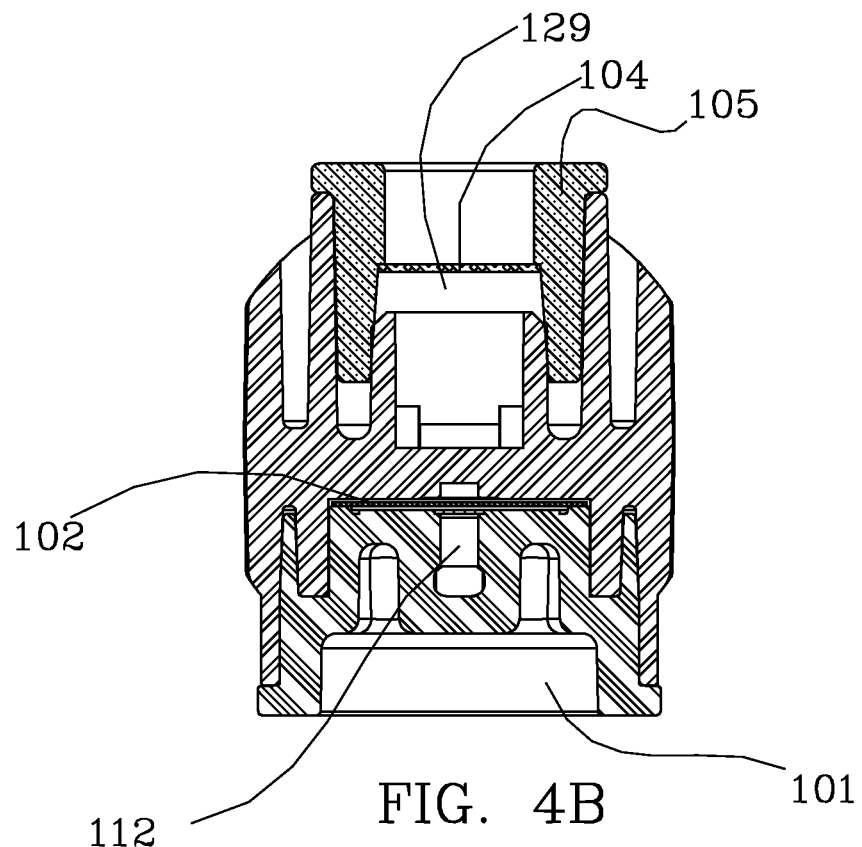
FIG. 4B is a cross section view of the embodiment of FIG. 3A shown along sectional plane 4B-4B normal to the cross section plane 2B-2B and opposite in direction to that of section plane 3B-3B.
Figure 4A:
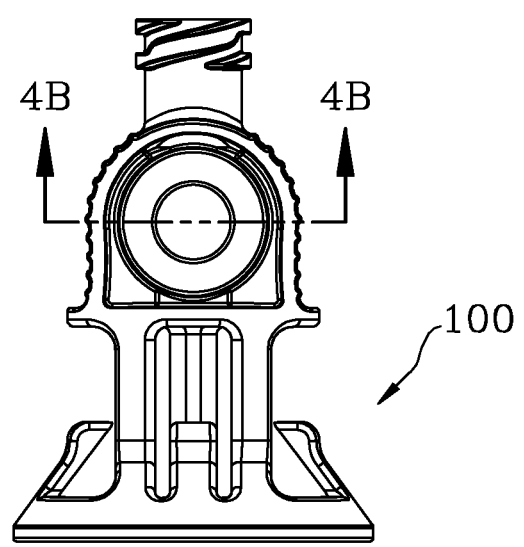
FIG. 4A is a perspective view of the vial access device of FIG. 3A, showing sectional plane 4B-4B.

Referring to FIGS. 4A and 4B, is a cross section view of the embodiment of FIG. 3A shown along sectional plane 4B-4B normal to the cross section plane 2B-2B and opposite in direction to that of section plane 3B-3B. Fluid conduit 112 is shown viewed up from its respective longitudinal axis. Fluid filter body 101 and fluid filter 102, as well as vent filter body 105 and vent filter 104 are shown in a press-fit or interference fit arrangement with upper housing 103.

Referring to FIGS. 5A, 5B, and 5C, vial access device 100 comprises a fluid filter body 101. Fluid filter body 101 includes first surface 120, configured as a first wall projecting from fluid filter body, show as an annular wall, but can be square or triangular, etc., to push filter body onto upper housing 103, via hand or automated assembly. One end of fluid conduit 117 forms an opening in first wall, which is one end of fluid conduit 117. Second surface 121, configured as a partial projecting wall shown of a shape corresponding to that of first surface 120 wall, but can be of any shape, e.g., square, triangular, etc., providing a tapered lead-in so as to axially center the fluid filter body engaging surfaces prior to assembly (e.g., via press fit) and to fill dead volume in the fluid path in upper housing 103. Partial opening in second wall is aligned with one end of fluid conduit 117 to fluidically connect the connector conduit with fluid conduit 117 via instantly formed fluid conduit 108 upon assembly of fluid filter body 101 with upper housing 103. Edge 118 of surface 121 provides a rotational lead in and key that aligns fluid conduit 117 with fluid conduit 108 of upper housing 103. Ridges 116 and dished surface 115 create a fluid path connecting the front surface 102a of filter 102 to fluid conduit 107 of fluid filter body 101. Surface 114, shown as annular ring, is used to secure fluid filter 102 to fluid filter body 101. Upper housing 103 can be configured to provide for indexing of fluid filter body 101 as discussed below.

This configuration avoids having to integrate the filter in the housing or with the spike. Thus, device 100 accommodates fluid filter 102 in a separate filter body 101 configured for assembly into the upper housing 103. In this configuration, where the filter body is separately constructed, the vial access device can be manufactured with a range of filters in a common filter body, e.g., filters of predetermined porosity and/or material (e.g., hydrophobic/hydrophilic), in the same manufacturing line, using the same equipment. In one aspect, a kit comprising the vial access device and an arrangement of filters in identical filter bodies, each with different filter material can be provided to a manufacturer or end-user.

Figure 6:
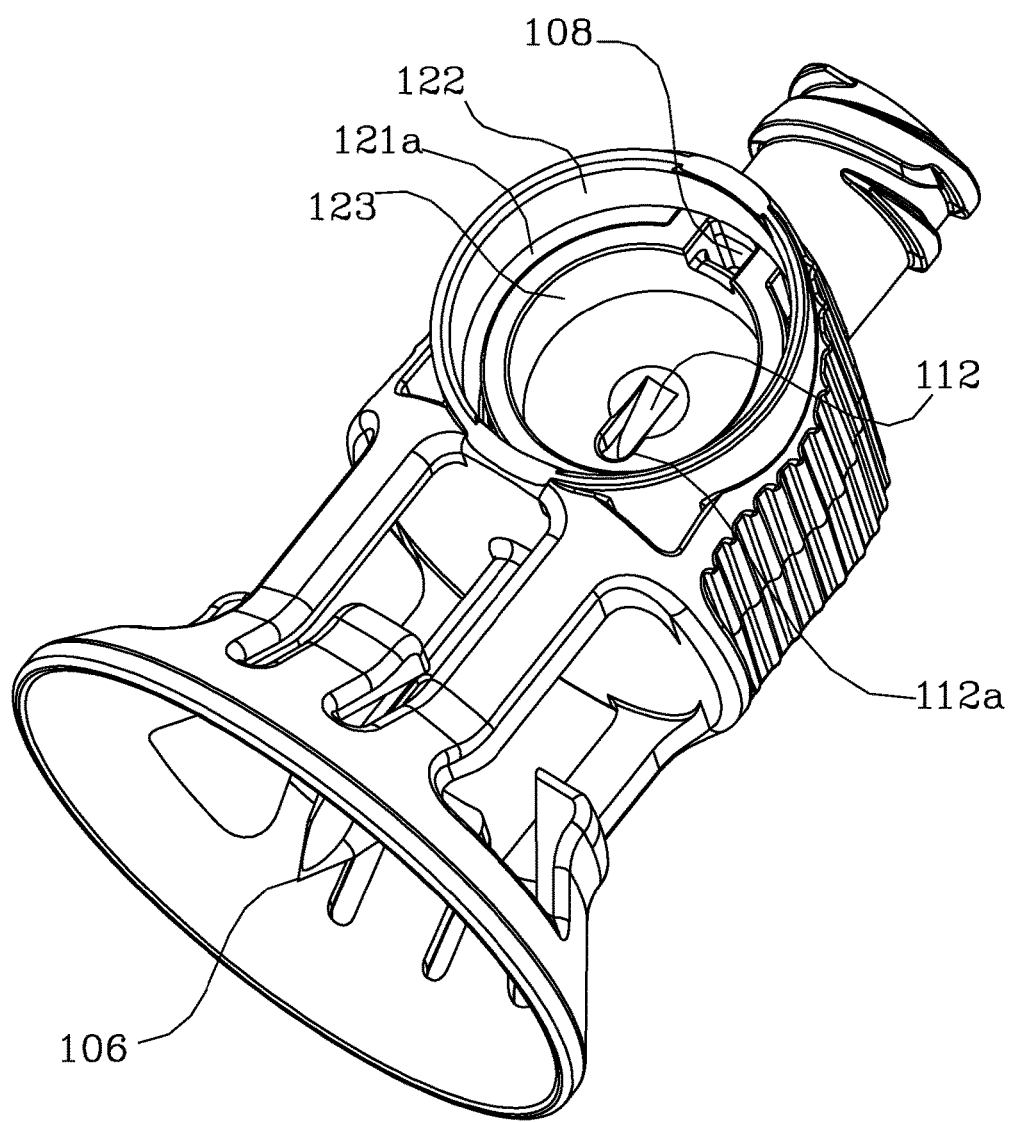
FIG. 6 is a perspective view of the vial access device of FIG. 1A with the filter body removed to show the upper housing.

Referring to FIG. 6, a perspective view of upper housing 103 with shroud 126 is shown. Inner annular surface 123 of upper housing 103 forms a seal with surface 110 of fluid filter body 101 (not shown). Outer annular surface 122 seals with surface 111 of filter housing. Opening 112a in upper housing (proximal end of fluid conduit 112 of spike 106) is configured to present fluid to front surface 102a of fluid filter 102 substantially parallel to the longitudinal axis of spike 106 and that of the fluid flow.

In using the vial access device 100, reference is now made to FIGS. 7A, 7B, and 7C, where vial 200 containing either a liquid, powered, and/or lypholized substance or a mixture having suspended particulate matter 137 in need of removal or reduction prior to transfer to a delivery device is attached to vial access device 100 and delivery device 133 connected to connector member 113 of upper housing 103. Vial 200 includes an upper, generally cylindrically shaped "necked" portion 200b over which shroud 126 of the vial access device 100 is received, vial 200 being held by fingers 125 of shroud 126. Delivery device 133 has volume 134 and fluid conduit 136 in communication with fluid conduit 108 of upper housing for delivery and/or withdraw of fluid from/ into volume 134. Show in detail in FIG. 7C, upon engagement of vial access device 100 with vial 200, spike 106 penetrates septum 201 of vial 200 and accesses the interior of vial 200. Vial 200 is securely held to vial access device 100 by fingers 125 which engage the rim of tapered neck portion 200b. In this configuration, fluid is delivered/transferred through fluid conduits 108, 107, fluid filter 102, and fluid conduit 112 of spike 106. Aspiration of vial 200 is provided via vent conduit 128 of spike 106 and vent filter 104 of vent filter body 105. As shown in FIG. 7CA, a fluid path is formed by elements of the upper housing 103, the fluid filter body 101, spike 106, and vial 200.

Although shown throughout the Figures, vent filter body 105 and/or vent filter 104 are optional to the function of vial access device 100. The embodiment as shown is for adapting the device, for example, to 13 mm or 20 mm vials.

Figures 8A, 8B:
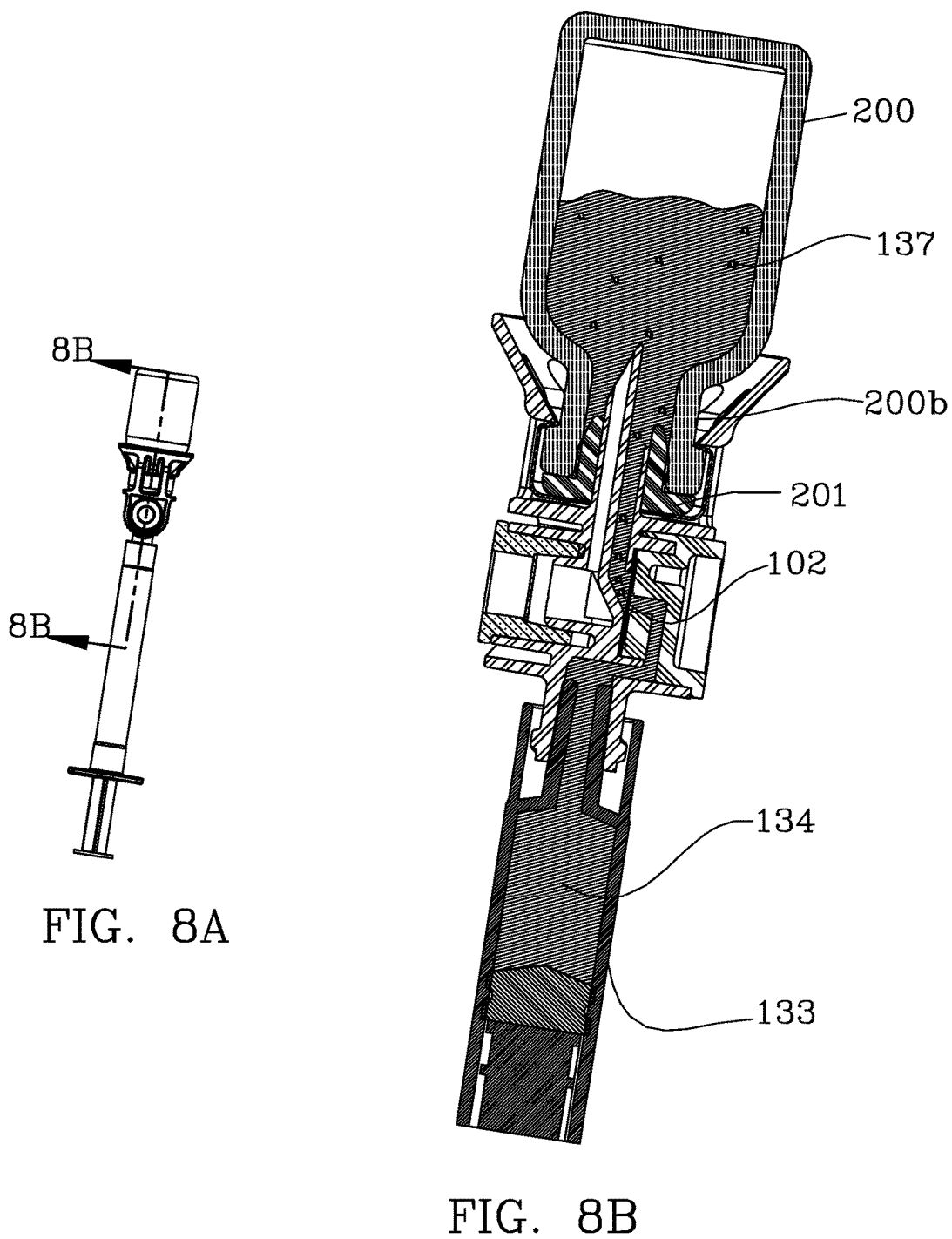
FIG. 8A is a side view of the vial access device of embodiment of FIG. 1A shown operatively connected to a vial and syringe with sectional plane 8B-8B shown.
FIG. 8B is a side cross section view of the vial access device as configured in FIG. 8A shown along sectional plane 8B-8B, showing the device connected to a vial of medicament with particulate and withdrawal of the medicament with reduced particulate into a syringe.

With reference to FIG. 8, once fluid is introduced to medicament in vial 200 and is thoroughly mixed, the contents of vial 200 can be withdrawn into volume 134 of delivery device 133, e.g. by withdrawing plunger rod of syringe. Because the fluid path is presented substantially parallel to the fluid filter surface 102a, particulate matter is retained in fluid filter 102 more efficiently, at least because of the increased surface area exposure of filter surface 102a and fluid.

Valve means, for example, flow control devices, can be integral or connectable to the connector member 113 of upper housing 103 so as to control fluid flow through the device. Such fluid control devices can include split septums, collapsible septums, valved male/female luers, stopcocks, and the like.

Figure 9A:
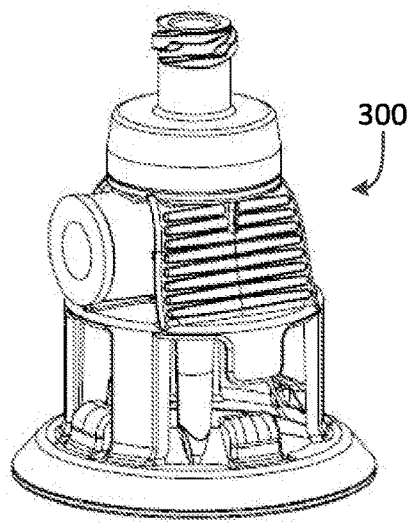
FIGS. 9A and 9B are perspective views, rotated 180 degrees of each other, respectively, of a vial access device embodiment of the device shown fully assembled.
Figure 9B:
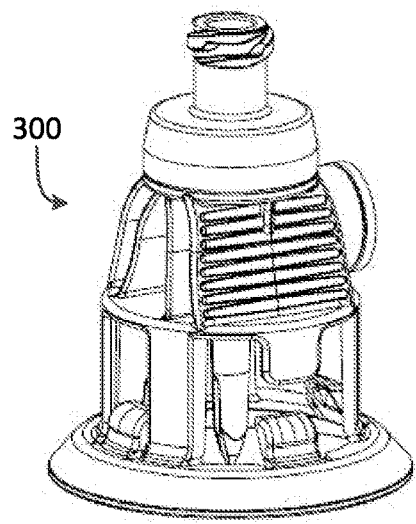
Figure 9C:
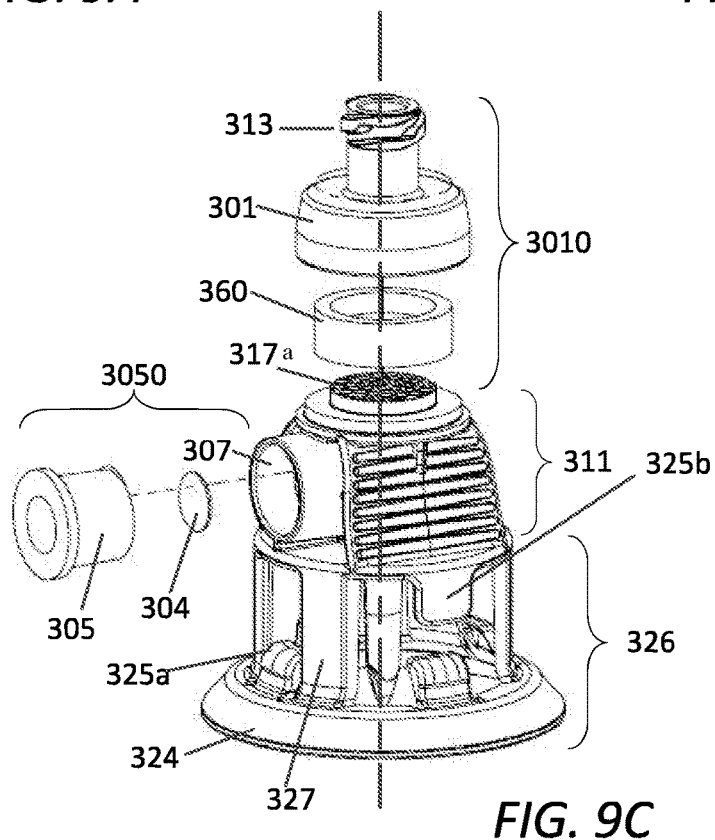
FIG. 9C is an exploded perspective view of the vial access device of FIG. 9A as disclosed and described herein.

Referring to FIGS. 9A and 9B, are shown a perspective view of an embodiment of device 300, shown in a fully assembled state. FIG. 9C is an exploded perspective view showing fluid filter assembly 3010 comprising fluid filter 317, retaining element 360, assembled with upper housing 311 configured to receive retaining element 360 and fluid filter 317 on surface 317a (as shown in more detail in FIG. 12) of upper housing 311. Connector member 313 projects from upper housing 311. Also shown is vent filter assembly 3050 comprising vent filter body 305 with corresponding vent filter 304 configurable into upper housing 311 via opening 307 for receiving fluid filter body 305 and fluid filter 304. Fluid filter assembly 3010 is configured to mate with upper housing 311. As shown in FIG. 9C, vent filter 304 surface is arranged essentially perpendicular to liquid filter 317 surface in the assembled device 300. Optional shroud 326 comprising extending features 327 terminating and in ring 324 with inwardly projecting finger element 325a and anti-snag tab 325b for securing device 300 to a vial or other medicament container.

Fluid filter 317 can consist of any appropriate material, micron porosity and efficiency for a given application. A typical range of micron porosity for a fluid filter is between about 0.2 uM and about 15 uM (micron). In one aspect, fluid filter 317 can be disk-shaped. Other shapes can be used for fluid filter 102.

Vent filter 304 can consist of any appropriate material, micron porosity and efficiency for a given application. A typical range of micron porosity for an vent filter is between 0.02 uM and 150 uM (micron). In one aspect, fluid filter 304 can be disk-shaped. Other shapes can be used for the vent filter 104.

Figure 9D:
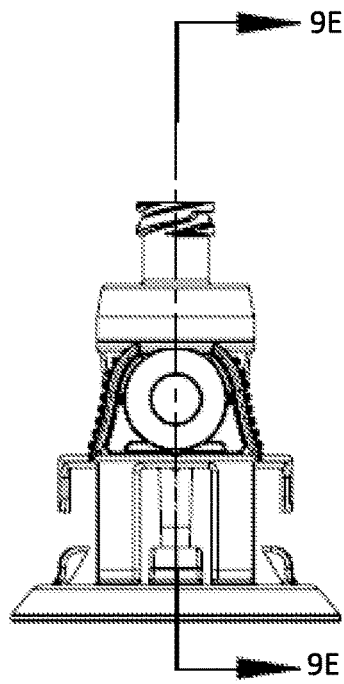
FIG. 9D is a side view of FIG. 9A, showing sectional plane 9E-9E.
Figure 9E:
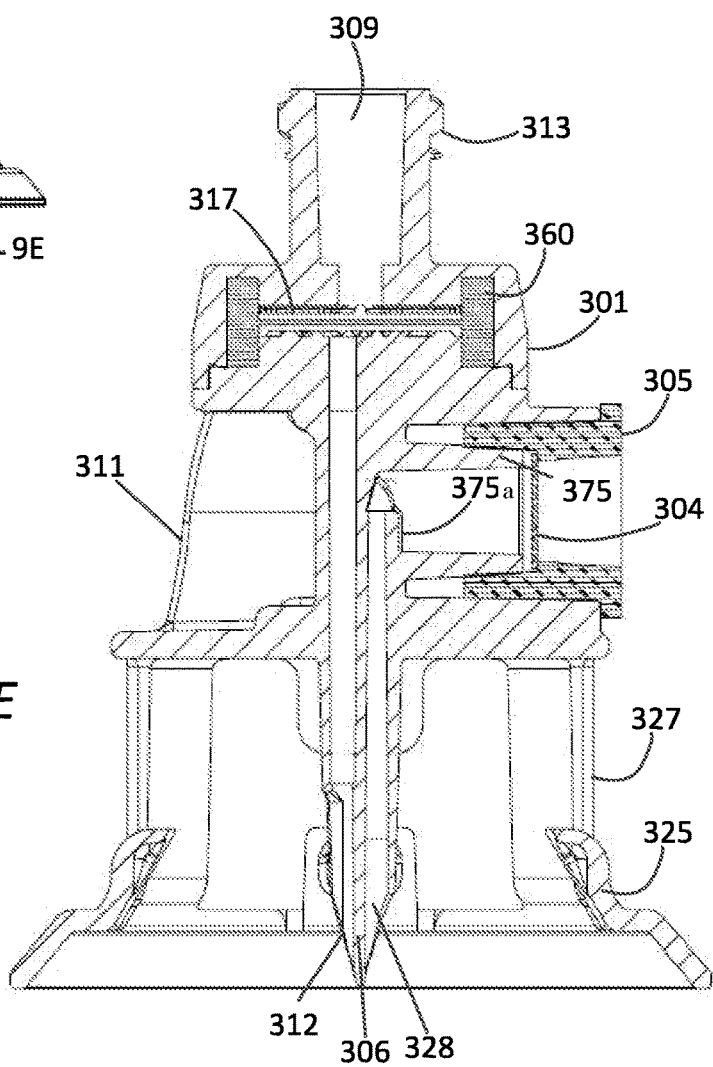
FIG. 9E is a side cross section view of the embodiment of FIG. 9D shown along section plane 9E-9E.

Referring to FIGS. 9D and 9E, FIG. 9D is a side view of device 300 and FIG. 9E is a side cross section view of the embodiment along sectional plane 9E-9E. Upper housing 311 comprises connector member 113 having fluid conduit 309 in fluid communication with a structured support 317a and upper housing 311. Vial access spike 306 provides a fluid path 312 from spike 306, through fluid filter 317 and into fluid conduit 309 through upper housing 311. In one aspect, fluid from a vial or connector is presented to a front surface of fluid filter 317 (not shown), the front face being substantially perpendicular to the direction of fluid flow and substantially perpendicular to the longitudinal axis of spike 306. Spike 306 includes vent conduit 328 communicating with vent filter body 305, filter 304, and ambient. Thus, as shown in FIG. 9E, face of fluid filter 317 is substantially perpendicular to face of vent filter 304. Element 375a provides for clearing the vent, e.g., preventing airlock if fluid enters void space between vent filter 304 and vent conduit 328. For example, if the vent becomes flooded, extending the orifice height with feature 375a aids in evacuating the fluid in an inverted orientation. Vent filter housing 305 is received by feature 375 and upper housing 311 to create a leak resistant or air-tight interference fit.

During use of the device 300, the direction of fluid flow is generally to/from fluid lumen 312 of spike 306 to connector conduit 309, a force to induce flow is created by a delivery device (e.g., syringe) attached to connector member 313. Connector member 313 can be a luer fitting or other threaded connector. The cross sectional area of the fluid path does not change significantly over this span so as not to inhibit flow or create pressure gradients within the device. Fluid filter 317 separates unfiltered fluid. Fluid filter assembly 3010 can be generally annular in shape, square, rectangular, oval, etc., provided it is configured to form a seal with upper housing 311 via various means including press fit, solvent bond, adhesive bond, ultrasonic bond, and/or via an additional elastomeric element such as an o-ring.

The fluid filter 317 may be attached to the fluid filter body 301 via adhesive, ultrasonic welding or insert molding. Alternately the fluid filter 317 may be held in place by a compression fit between the upper housing 311 and the fluid filter body 301 Alternately, the fluid filter 317 may be attached to the retaining element 360.

In one aspect, the fluid filter is a particulate-filtering sheet with a defined perimeter having extending walls from one or both surfaces of the sheet. The extending walls 361a, 361b, can extend the same distance or different distances from the sheet, and/or one extending wall can be flush with the sheet surface. Thus, referring to FIG. 10, an exploded view of fluid filter assembly 3010 is shown with retaining element 360 and fluid filter 317a. Fluid filter body 301 is shown as a projecting wall configured to receive retaining element 360. FIG. 11 shows a sectional view along sectional plan 11-11, with retaining element 360 with extending walls 361a, 361b supporting fluid filter 317, configured as a sheet. In one aspect, a sheet of suitable particulate-filtering material is inserted into an injection mold tool and retaining element 360 is over-molded on the perimeter of the sheet. The retaining element 360 can be constructed of plastics such as polyolefins, styrenics, and the like. The resultant fluid filter 317 can then be press fit, glued, heat staked, or ultrasonically welded, etc, into position, either on the upper housing 311, or within the fluid filter body 301, for example, on or around dished surface 315. Fluid filter body 301 and retaining element 360 can be annularly shaped, as shown in FIG. 10, or can be square-, rectangular-, or oval-shaped. The fluid filter 317 can be constructed of a nonwoven media or a woven screen of natural or synthetic materials, such as rayon, cellulose, polyolefins, nylons, and the like. Typical particulate filtration ranges for the fluid filter would be about 5 to about 20 micron, but can be higher or lower. In this manner, the filter material can be selected as needed, and/or replaced with minimal re-tooling in the assembly of the fluid filter assembly for particular uses.

Raised dish surface 315 can be sized to accommodate retaining element 360, e.g., tolerance fit about the inner projecting wall of fluid filter body 301, and like features 3170, prevent filter material from sealing off against a flat surface. Raised dished surface 315 can comprise ridges for supporting fluid filter 317*a*. Alternately, the non-woven or woven media can be die cut and directly heat staked, welded, crimped, or otherwise adhered in position without the overmolded perimeter to either the upper housing 311, or to the fluid filter assembly 3010 before being joined together with the upper housing 311. Thus, FIG. 12 shows an alternate embodiment of a fluid filter element, thus, fluid filter 317*b* having raised surface elements 3170, e.g., compressive bubbles or bumps surrounding conduit 309*a* that is configured to be attached to the top of the upper housing 311 and arranged for conduit 309*a* to align with fluid lumen 312. Such elements 3170 can be molded in or stamped, for example. FIG. 13 shows another embodiment of a fluid filter element, thus fluid filter 317*c* is shown of an essentially smooth solid construction.

Figure 14A:
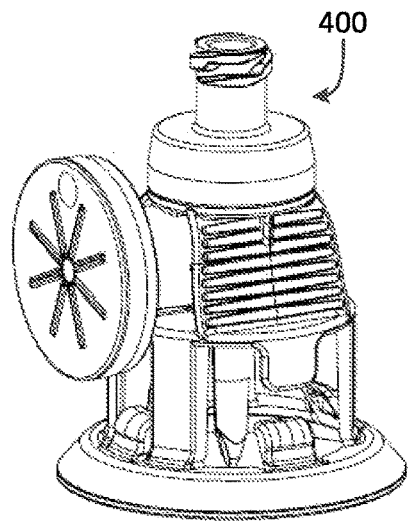
FIGS. 14A and 14B are perspective views, rotated 180 degrees of each other, respectively, of a vial access device embodiment of the device shown fully assembled.
Figure 14B:
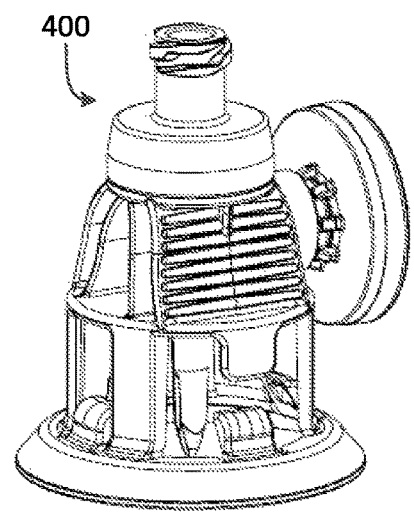
Figure 14C:
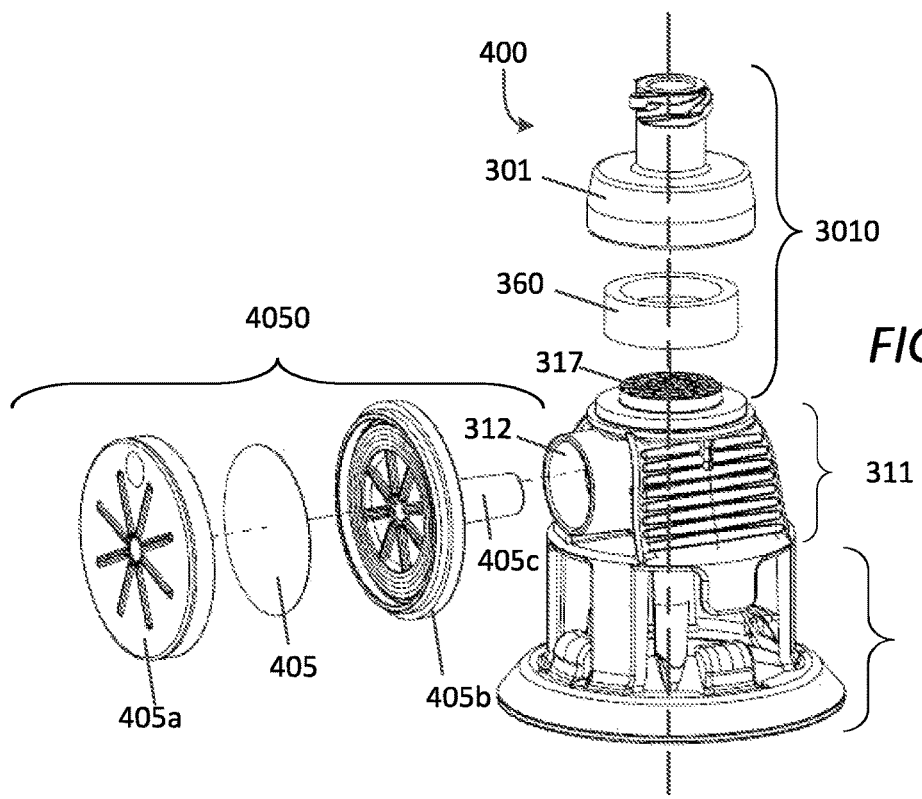
FIG. 14C is an exploded perspective view of the vial access device of FIG. 14A as disclosed and described herein.

Referring to FIGS. 14A-14C, side views and exploded perspective views of an alternate embodiment device 400 is shown, generally similar to that of device 300, but for vent filter assembly 4050 being of larger total surface area, having front cover element 405*a* arranged to mate with back cover element 405*b* and contain vent filter 405. Back cover element of vent filter assembly 4050 has conduit 405*c* for insertion into opening 307 of upper housing 311 for mating with housing 311 via press fit, solvent bond, adhesive bond, ultrasonic bond, and/or can contain an additional elastomeric element such as an o-ring. Vent filter assembly 4050 can be configured for reversible attachment/detachment.

Figure 15A:
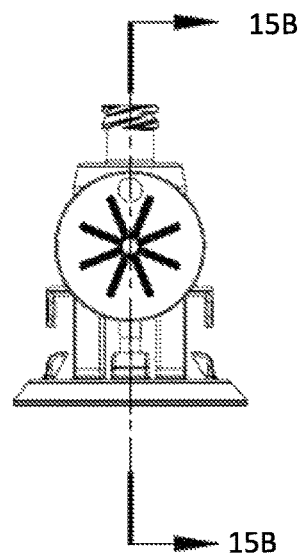
FIG. 15A is a side view of FIG. 14A, showing sectional plane 15B-15B.
Figure 15B:
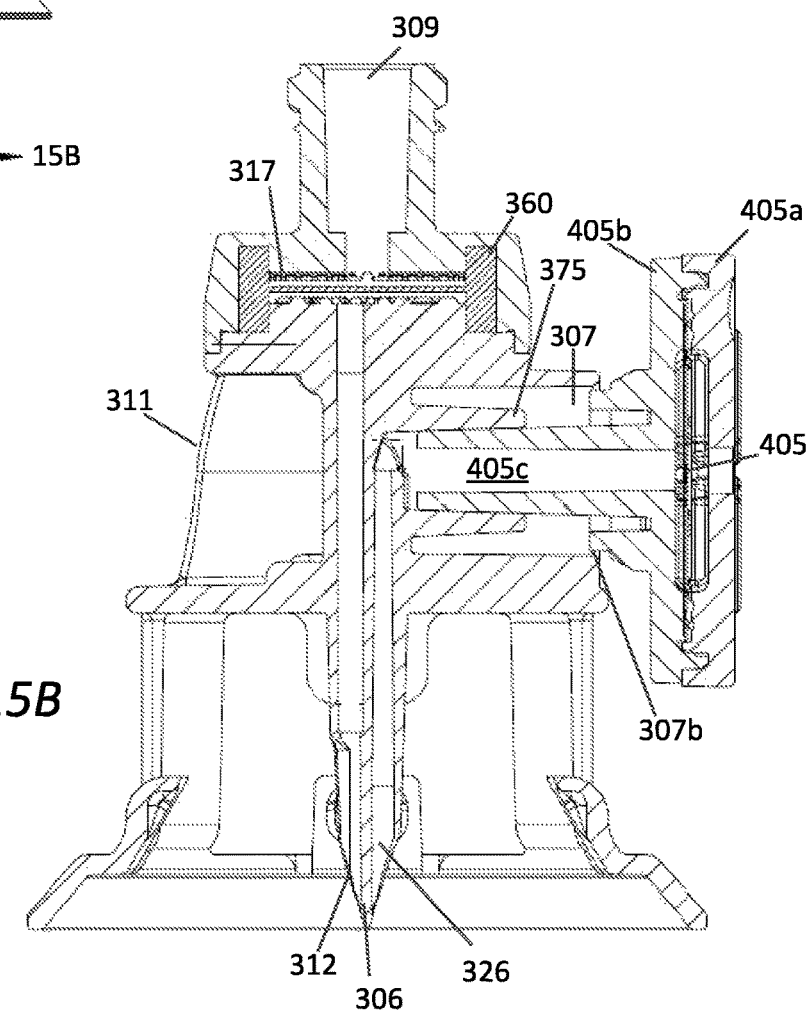
FIG. 15B is a side cross section view of the embodiment of FIG. 15A shown along section plane 15B-15B.

With reference to FIGS. 15A and 15B, showing cross sectional view of device 400 along sectional plane 15B-15B, Vent filter assembly 4050 can be mated or otherwise sealed to upper housing 311 at interference point 307*b*, with conduit 405*c* being received by element 375 to secure conduit 405*c* to upper housing 311 and/or provide a leak resistant or air-tight seal to housing 311.

upper housing 103 with shroud 126 is shown. Inner annular surface 123 of upper housing 103 forms a seal with surface 110 of fluid filter body 101 (not shown). Outer annular surface 122 seals with surface 111 of filter housing. Opening 112*a* in upper housing (proximal end of fluid conduit 112 of spike 106) is configured to present fluid to front surface 102*a* of fluid filter 102 substantially parallel to the longitudinal axis of spike 106 and that of the fluid flow.

In using the vial access device 300 and 400, reference is now made to FIGS. 16A-16C, where vial 200 containing either a liquid, powered, and/or lypholized substance or a mixture having suspended particulate matter 137 in need of removal or reduction prior to transfer to a delivery device is attached to vial access device 300 and delivery device 133 connected to connector member 313 of upper housing 103.

Vial 200 includes an upper, generally cylindrically shaped "necked" portion 200*b* over which shroud 126 of the vial access device 100 is received, vial 200 being held by fingers 125 of shroud 126. Delivery device 133 has volume 134 and fluid conduit 136 in communication with fluid conduit 309 of upper housing 311 for delivery and/or withdraw of fluid from/into volume 134. Show in exploded detail in FIG. 16C, upon engagement of vial access device 300 with vial 200, spike 306 penetrates septum 201 of vial 200 and accesses the interior of vial 200. Vial 200 is securely held to vial access device 300 by fingers 325 of shroud which engage the rim of tapered neck portion 200*b*. In this configuration, fluid is delivered/transferred through fluid lumen 312 of spike 306 and fluid filter 317. Aspiration of vial 200 is provided via vent conduit 328 of spike 306 and vent filter 304 of vent filter body 305. A similar use is provided with device 400 as that described for device 300.

Although shown throughout the Figures, vent filter body 105 and/or vent filter 104 are optional to the function of vial access device 100. The embodiment as shown is for adaptable, for example, to 13 mm or 20 mm vials.

Figures 17A, 17B:
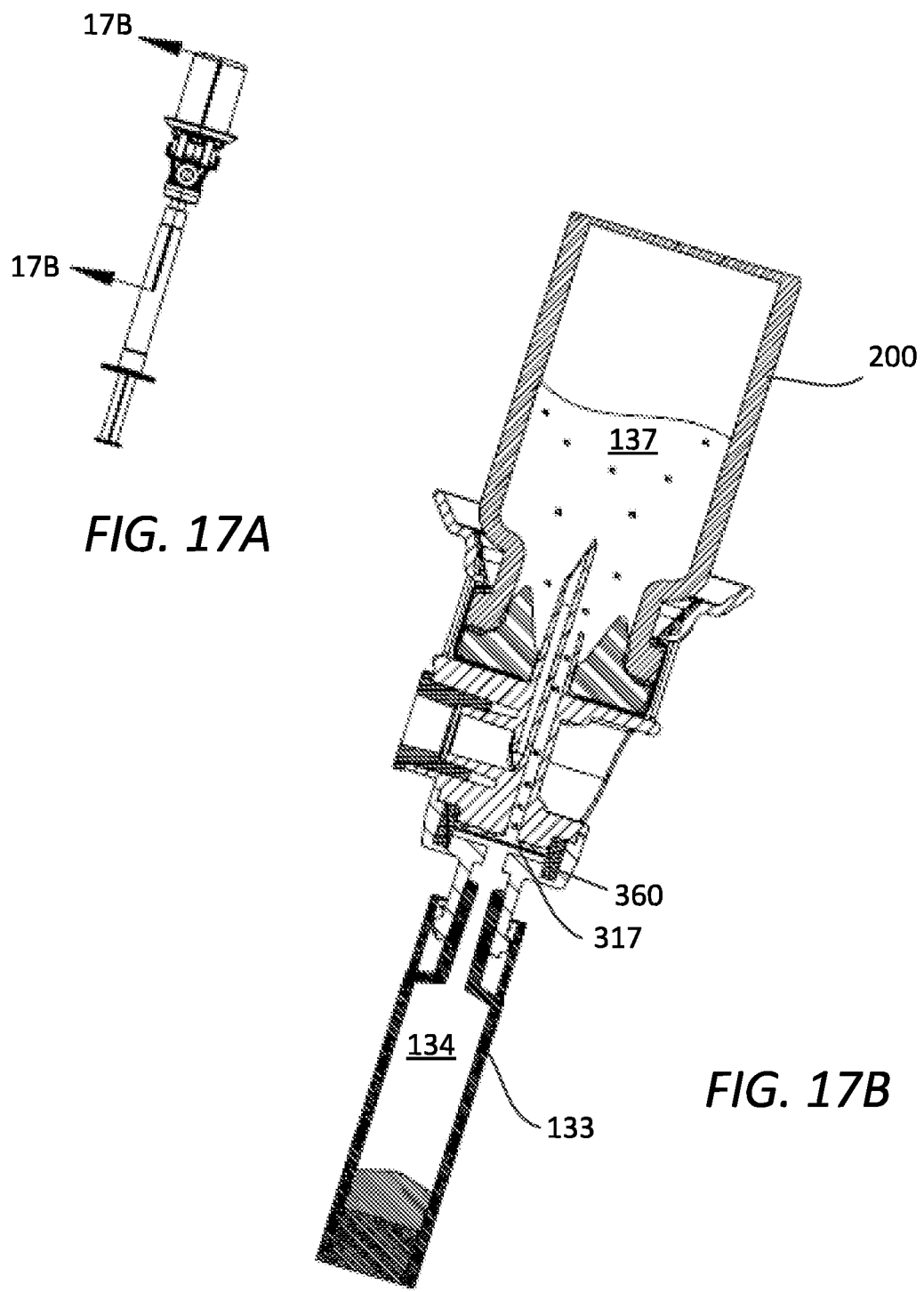
FIG. 17B is a side cross section view of the vial access device as configured in FIG. 17A shown along sectional plane 17B-17B, showing the device connected to a vial of medicament with particulate and withdrawal of the medicament with reduced particulate into a syringe.

With reference to FIGS. 17A and 17B, once fluid is introduced to medicament in vial 200 and is thoroughly mixed, essentially particle-free contents of vial 200 can be withdrawn into volume 134 of delivery device 133, e.g. by withdrawing plunger rod of syringe. Because the fluid path of device 300 presents the mixed fluid substantially perpendicular to the fluid filter 317 surface particulate matter is retained efficiently, and filter 317 is provided additional structural support via retaining element 360, thus preventing or eliminating rupture of filter 317 during use.

Valve means, for example, flow control devices, can be integral or connectable to the connector member 313 of upper housing 311, so as to control fluid flow through the device 300, 400. Such fluid control devices can include split septums, collapsible septums, valved male/female luers, stopcocks, and the like.

We claim:

1. A vial access device comprising
   (i) an upper housing comprising:
      a connector member for receiving a medicament delivery device, the connector member having a fluid conduit in fluid communication with the upper housing; and
      a bottom surface;
   (ii) a spike having a proximal end and a distal end, the proximal end projecting from the bottom surface of the upper housing, the spike having at least one lumen arranged parallel to a first longitudinal axis, the at least one lumen connecting the proximal end of the spike with the distal end, the at least one lumen being in fluid communication with the upper body;
   (iii) a fluid filter body comprising
      a fluid filter having a front surface to be contacted by fluid from the at least one lumen, the front surface aligned with the first longitudinal axis and substantially parallel to the direction of fluid flow in the at least one lumen, the fluid filter body further comprising a first fluid conduit in contact with a back surface of the fluid filter, the first fluid conduit is non-parallel with the first longitudinal axis and in communication with a second fluid conduit, the second fluid conduit in fluid communication with the fluid conduit of the connector member;
   (iv) optionally, a vent body and vent filter;
   (v) optionally, a lower housing connected to the upper housing, the lower housing having a shroud projecting therefrom and at least partially surrounding a portion of the spike; the shroud configured to receive a vial or container.

2. The device of claim 1, wherein the second fluid conduit aligned substantially parallel to the first longitudinal axis.

3. The device of claim 1, wherein the fluid filter body comprises a substantially cylindrical shape having a first end configured to be received in the upper housing, and a second end, the back surface of the fluid filter being circumferentially mounted on the first end of the filter body.

4. The device of claim 1, wherein the fluid filter body comprises
- a first surface configured as an inner wall projecting from the fluid filter body and having an opening at a base in the inner annular wall fluidically coupled to the first fluid conduit and providing alignment of the connector conduit with the first fluid conduit upon assembly with the upper housing; and
- a second surface, configured as a partial wall projecting from the fluid filter body and partially surrounding the inner wall, the partial wall configured to fill dead volume in the upper housing,
- wherein, upon assembly of the fluid filter body with upper housing, a fluid channel is formed providing fluid communication between the connector conduit and the first conduit.

5. The device of claim 4, wherein the fluid channel is substantially parallel to the first fluid conduit and substantially non-parallel with the second fluid conduit, the connector conduit, and the at least one lumen of the spike.

6. A method of filtering particulate material from a reconstituted medicament, the method comprising:
- providing a vial access device as defined in claim 1;
- providing at least one of a vial comprising reconstituted or reconstitutable medicament and/or a delivery device selected from a syringe, IV bag, or IV line; and
- filtering the reconstituted or reconstitutable medicament.

7. A vial access device comprising
- (i) a fluid filter assembly comprising:
  - a connector member for receiving a medicament delivery device, the connector member providing fluid communication with medicament delivery device
  - a housing containing a fluid filter;
- (ii) an upper housing receiving the fluid filter assembly at a top surface, the upper housing comprising
  - a spike having a longitudinal axis and a proximal end and a distal end, the proximal end projecting from a bottom surface of the upper housing, the spike having at least one lumen arranged parallel to the longitudinal axis, the at least one lumen connecting the proximal end of the spike with the distal end, the at least one lumen being in fluid communication with the fluid filter; and
  - an opening receiving an vent filter body with vent filter;
  - the fluid filter having a front surface aligned non-parallel with the longitudinal axis and substantially perpendicular to the direction of fluid flow in the at least one lumen, and the vent filter surface positioned essentially perpendicular to the fluid filter surface;
- (iv) optionally, a shroud projecting therefrom and at least partially surrounding a portion of the spike; the shroud configured to receive a vial or container.

8. The vial access device of claim 7, wherein the fluid filter is a particulate-filtering sheet with a defined perimeter, the perimeter having extending walls from one or both surfaces of the sheet.

9. The vial access device of claim 8, wherein the particulate-filtering sheet is overmolded with a plastic.

10. A vial access device comprising:
- a fluid filter assembly having a fluid connecter, a fluid filter
- an upper housing receiving the fluid filter assembly and in fluid communication with the fluid connector of the fluid filter housing, the upper housing comprising;
- a vent filter body with vent filter;
- a vial access spike projecting from the upper housing;
- the fluid filter in fluid communication with the vial access spike and the fluid connector, the fluid filter having a fluid filter surface substantially non-parallel to the direction of fluid flow through the access spike, and a vent filter having a vent filter surface essentially perpendicular to the fluid filter surface.

11. The vial access device of claim 10, wherein the fluid filter is a particulate-filtering sheet with a defined perimeter, the perimeter having extending walls from one or both surfaces of the sheet.

12. The vial access device of claim 11, wherein the particulate-filtering sheet is overmolded with a plastic.

13. The vial access device of claim 11, wherein the particulate-filtering sheet is a woven or nonwoven synthetic or natural material.

14. The device of claim 10, wherein the vent filter body comprises a substantially cylindrical shape having a first end configured to be received in the upper housing, and a second end, a back surface of the vent filter being circumferentially mounted on a first end of the filter body.

15. The vial access device of claim 10, wherein the fluid filter is a particulate-filtering sheet with a defined perimeter, the perimeter having extending walls from one or both surfaces of the sheet.

16. The vial access device of claim 15, wherein the particulate-filtering sheet is overmolded with a plastic.

* * * * *

UNITED STATES PATENT AND TRADEMARK OFFICE
CERTIFICATE OF CORRECTION

PATENT NO. : 9,585,812 B2  
APPLICATION NO. : 14/377437  
DATED : March 7, 2017  
INVENTOR(S) : Edward P. Browka et al.

Page 1 of 1

It is certified that error appears in the above-identified patent and that said Letters Patent is hereby corrected as shown below:

On the Title Page

Item (72) Inventors:

Please change the information for the third inventor to:

Gianni Guala, Torino (IT)

Signed and Sealed this  
Thirtieth Day of May, 2017

Michelle K. Lee  
*Director of the United States Patent and Trademark Office*